United States Patent [19]

Sherry et al.

[11] Patent Number: 5,407,269
[45] Date of Patent: Apr. 18, 1995

[54] DYNAMIC MIXING CHAMBER

[75] Inventors: Robert W. Sherry, Burlington; Douglas W. Towne, Colchester, both of Vt.

[73] Assignee: International Business Machine Corporation, Armonk, N.Y.

[21] Appl. No.: 910,945

[22] Filed: Jul. 9, 1992

[51] Int. Cl.⁶ .................................................. B01F 5/04
[52] U.S. Cl. .................................. 366/174.1; 366/340; 73/1 R
[58] Field of Search ............... 366/150, 167, 173, 177, 366/338, 340, 174; 604/83, 86, 88; 137/605; 251/149.1; 73/1 G, 1 R, 865.5; 285/3, 334.3, 417; 324/71.4, 71.1

[56] References Cited

U.S. PATENT DOCUMENTS

| | | | |
|---|---|---|---|
| 3,669,542 | 6/1972 | Capellaro | 356/336 |
| 3,794,299 | 2/1974 | Wagner | 366/173 |
| 3,869,208 | 3/1975 | Lorenz | 356/336 |
| 3,955,833 | 5/1976 | Silbert | 285/3 |
| 4,058,363 | 11/1977 | Silbert | 285/3 |
| 4,193,288 | 3/1980 | Berber et al. | 73/1 R |
| 4,331,862 | 5/1982 | Ryan | 377/29 |
| 4,585,435 | 4/1986 | Vaillancourt | 604/83 |
| 4,596,036 | 6/1986 | Norgren et al. | 377/10 |
| 4,653,078 | 3/1987 | Aritomi et al. | 377/10 |
| 5,041,087 | 8/1991 | Loo et al. | 604/83 |

FOREIGN PATENT DOCUMENTS

| | | | |
|---|---|---|---|
| 960932 | 1/1975 | Canada | 604/83 |
| 47911 | 11/1979 | European Pat. Off. | 604/83 |
| 0111723 | 6/1984 | European Pat. Off. | 604/86 |
| 302344 | 12/1988 | Japan | 73/1 R |
| 2053000 | 2/1981 | United Kingdom | 604/83 |

Primary Examiner—David A. Scherbel
Assistant Examiner—Tony G. Soohoo
Attorney, Agent, or Firm—James M. Leas

[57] ABSTRACT

The dynamic serial dilution apparatus of the invention, consists of an injection/mixing chamber and a precision injector from which foreign material may be impelled into a flowing fluid leading to the device to be calibrated. This arrangement allows the controlled injection of a concentrate of foreign material into pressurized piping systems with a negligible level of incidental undesirable artifacts. The injection/mixing chamber assures even dilution of the concentrated stock solution and thorough mixing with the carrier fluid without adding undesirable artifacts. As a result, the particle counter being tested sees only a dilute, homogeneous sample of specific, known concentration. Altering the delivery rate of the stock contaminant solution or the flow volume of the carrier fluid permits the particle concentration in the sample to be easily varied. The carrier fluid, typically deionized water, can revert instantly to a condition free of foreign material upon cessation of the foreign material injection.

15 Claims, 2 Drawing Sheets

DYNAMIC MIXING CHAMBER

BACKGROUND OF THE INVENTION

This invention relates generally to mixing chambers and more specifically to a dynamic mixing chamber for introducing known levels of a specific foreign material to a flow of fluid having an established purity level to provide a standard of testing of particle counters and other devices used to monitor contaminant levels in flowing fluids.

FIELD OF THE INVENTION

Proper testing and characterization of particle counters for use in liquids requires repeatable presentation of a standardized particle suspension or a specific foreign material to the instrument being tested. The standard suspension, of known particle size and concentration, must be measurable by other certified methods and free of incidental contamination of unknown type and/or concentration (artifacts) which would elicit spurious responses from the instruments during testing.

Prior art liquid particle sensors have sensitivities that permit detection of particles as small as 50 nanometers (nm) present at concentrations less than one hundred particles per milliliter. Described as the ratio of particle volume to liquid volume this equates to less than 1 part per ten trillion ($10^{-12}$). Preparation of test standards for these instruments requires consummate precision to assure concentration accuracy and freedom from incident artifacts. Correct scientific practice requires a statistically significant number of data points be collected for test validity. The test apparatus and technique chosen is obliged to be able to consistently deliver a standard containing known concentrations of detectable particles or foreign material to the instrument for the duration of the test and must be repeatable at will to assure the accuracy of future recalibrations and allow characterization studies of instrument reliability, repeatability, drift, and useful life.

invariably it is necessary to test instrument sensitivity at different ranges, consequently, the concentration of the standard solution containing the detectable particles or foreign material should be easily and predictably alterable to higher or lower levels without loss of accuracy. Testing an instrument's freedom of concentration from spurious induced responses in a dynamic state necessitates a test apparatus that can rapidly return the test fluid to a particle free or foreign material free condition without interruption of flow. Finally testing must be able to be carried out in a cost effective manner that does not require complex secondary measurement to certify the accuracy of each test segment.

There are three contemporary methods used for testing liquid particle counters. All utilize a finite volume of particle suspensions mixed to a fixed concentration and vary only in the manner in which this solution is introduced to the particle counter: gravity feed, pumped injection, and vacuum aspiration. These bulk volume methods have major problem areas.

Since they depend on individual batches of test solution each batch of test solution of particles or foreign material must be precisely mixed using multiple serial dilutions. The uncertainties introduced when diluting the stock solution from approximately $10^{13}$ particles per milliliter to a large volume of test solution containing less than $2 \times 10^3$ particles per milliliter results in each batch of the test solution being unique and non-reproducible. Also, the concentration of each batch must be certified, an expensive proposition. Second, the components of the delivery system contribute to the measurement uncertainty. The large test solution vessel is difficult to clean but easily contaminated; and the actions of the components of the delivery system can cause considerable variations in the numbers of particle events detected by the particle counter.

For example, if polystyrene latex (PSL) spheres are the particles to be used as the injected foreign material and the fluid is deionized water reducing the concentration of the bulk solution of foreign material can and usually does increase the frequency of counts from incident artifacts with respect to the total counts.

The use of a prior art gravity fed bulk test solution is dependent upon being able to mount the vessel high enough to overcome the flow resistance of the piping system and the particle counter being tested. Obviously, the larger the vessel, the longer the testing period but physical restraints and the sampling rate of the particle counter combine to limit the testing period. Baseline restoration (e.g. returning to a foreign material free carrier stream) is possible only if flow of the carrier stream is stopped and the piping switched to a clean carrier stream source.

Installing a pump between the test vessel and the particle counter does not eliminate all the problems of the gravity feed method and adds further problems in that the pump has been added as another source of artifacts. Uncertainty is also added due to the pressure and flow fluctuations caused by the pump.

Locating the pump downstream of the particle counter, eliminates the introduction of artifacts from a pump, but causes the solution to enter the particle counter at a reduced pressure which can lead to the formation of bubbles in the test solution resulting in specious particle counts.

SUMMARY OF THE INVENTION

The present invention which uses dynamic serial dilution, is a vast improvement over the prior art.

The dynamic serial dilution apparatus of the invention, consists of an injection/mixing chamber and a precision injector from which foreign material may be impelled into a flowing fluid leading to the device to be calibrated. This arrangement allows the controlled injection of a concentrate of foreign material into pressurized piping systems with a negligible level of incidental artifacts. The injection/mixing chamber assures even dilution of the concentrated stock solution and thorough mixing with the carrier fluid without adding artifacts. As a result, the particle counter being tested sees only a dilute, homogeneous sample of specific, known concentration. Altering the delivery rate of the stock contaminant solution or the flow volume of the carrier fluid permits the particle concentration in the sample to be easily varied. The carrier fluid, typically deionized water, can revert instantly to a condition free of foreign material upon cessation of the foreign material injection.

An object of the invention is to provide a dynamic mixing chamber for introducing foreign material into an ultra-filtered, ultra-pure fluid delivery system having an output which can be coupled to test instruments or liquid particle sensors either in parallel or in series to provide continuous calibration of and accurate comparison between the instruments.

A further object of the present invention permits the introduction of a standard concentrate of foreign material from a certified source which is metered in and mixed with a pure filtered carrier liquid or fluid while avoiding pressure fluctuations and other disturbances which can influence the test results.

Still another object of the present invention permits the dilution ratio of the introduced standard to be readily and predictably altered to match the calibration requirements of the instrument at hand.

The injection chamber of the present invention assures that dilution and mixing of the foreign material with the carrier fluid is without adverse effects and can be operable for a fixed period of time without interruption. Moreover, the invention can be easily and predictably varied so that the fluid flow will revert instantly to a state, free of foreign material, as soon as the injection of the foreign material into the fluid flow ceases.

The present invention avoids all the known problems of the prior art and utilizes a mechanism that permits injection of a preselected certified concentration of foreign material into a high pressure system with exact delivery of the foreign material to provide constant and repeatable testing and calibration under the same fluid and pressure conditions encountered in an industrial field application. In addition, any contaminant which is soluble or suspendable in a carrier fluid can be prepared or certified as a standard for calibration of fluid monitoring instrumentation by dynamic serial dilution as taught by the present invention.

DESCRIPTION OF THE PREFERRED EMBODIMENT

Figure 1:
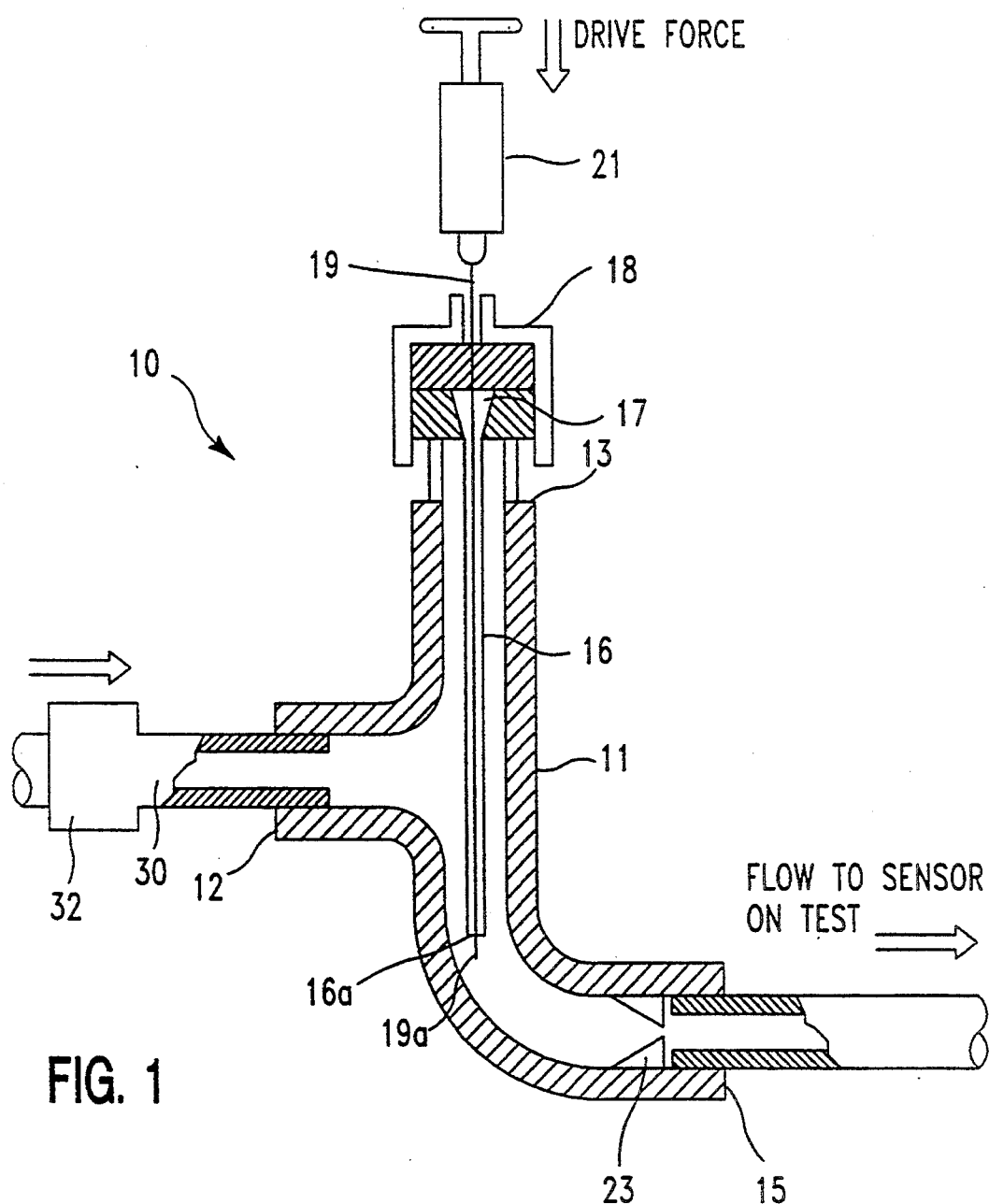
FIG. 1 shows a schematic of the preferred embodiment of the invention.
Figure 2:
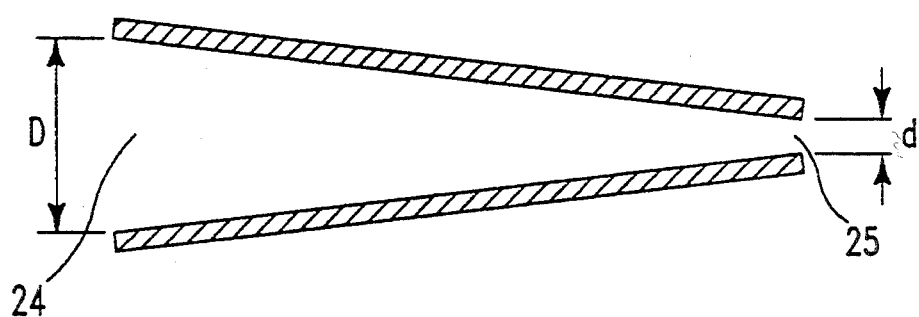
FIG. 2 shows the mixing nozzle used in the apparatus of FIG. 1.

FIG. 1 shows the preferred embodiment of the mixing chamber 10 of the present invention. Chamber 10 is generally comprised of a body 11 provided with an inlet orifice 12, through which a clean undiluted carrier fluid, such as deionized water, is transmitted into the mixing chamber from a suitable source (not shown), an entrance aperture 13, through which an impurity can be introduced into the fluid stream and at least one outlet orifice or tube 15 through which the fluid exits the mixing chamber. Preferably, the mixing chamber 11 is made of a plastic such as perfluoroalkoxy (PFA). This PFA material is desirable because it is chemically stable and does not introduce artifacts into the fluids passing there through. Affixed to the entrance aperture 13 is a hollow guide 16 covered by a sealing septum 17, generally comprised of a soft resilient material, such as rubber, which will seal the hollow guide 16 held in place by a cap 18 which has a centrally located aperture therein that lines up with the guide 16. An injector 21, which may be in the form of a syringe and containing a selected concentrate of foreign material to be introduced in the carrier fluid, is positioned over and coupled to the cap 18 so that a hollow injection tube 19 of selected size can pass from the reservoir 21 through the sealing septum 17 and into and through the guide 16. The tip 19a of the tube 19 must emerge from and extend below the end 16a of the guide 16. In the present invention it has been found that the tip 16a of the guide 16 must be positioned a sufficient distance below the center line of the inlet 12 to assure that no cross currents or turbulent flow is produced around the tip 19a of the tube 19 through which the foreign material is introduced into the pure fluid stream. Preferably, this position of the tip 16a of the tube 16 is positioned below the center line of inlet 12 a distance equal to approximately four times the inner diameter of the inlet orifice and can be positioned at a distance equal to as much as twelve times the diameter of the orifice. Similarly, the tip 19a of the tube 19 through which the foreign material is actually introduced into the flowing stream is also positioned below the center line of the inlet 12 a distance approximately equal to seven to fifteen times the inner diameter of the inlet 12. By so positioning the tip 19a of the tube 19 a sufficient distance from the center line of the inlet 12 it is assured that no turbulence or other non-laminar flow is created in the flow of the introduced carrier fluid when the carrier fluid is coming in in a laminar flow with a Reynolds number of 500 or less. Positioned beyond the tip 19a, of the tube 19, a minimum length of one inlet inner diameter from the tip of the tube 19a, is a mixing nozzle 23. This nozzle is particularly shown in FIG. 2 and is tapered with an inlet diameter 24 substantially equal to the diameter of the tube in which it is inserted and an exit diameter 25 approximately equal to 14% of the nozzle inlet 24. All the fluid exiting the system passes through the nozzle before reaching the outlet tube 15. The taper of this nozzle is preferably such that the length of the nozzle is 5–6 times the diameter of the outlet tube 15. This nozzle provides the fluid with a Reynolds number of between 5,000 and 6,000. This high Reynolds number, at the mouth of the orifice, causes adequate mixing of the foreign material in the carrier fluid to occur downstream from the nozzle in the exit tube 15 and a well mixed stream is created. A Reynolds number lower than 5,000 results in poor or no mixing and a Reynolds number higher than 6,000 produces so much pressure drop within the mixing chamber as to create undesirable or non-interpretive results.

These specific dimensions of the actual unit used was the entrance orifice 0.25 inches ID (inner diameter), the exit orifice was 0.25 inches ID, the tube 19 was a 28 gauge ID and the guide 16 had a 100 gauge ID. The distance at the tip of **19*a* of the tube 19, was from the center line of the entrance orifice 12**, 1.78 inches while the tip of the exit of the mixing nozzle was 2¼ inches from the central line of the entrance orifice. The mouth of the nozzle pad had an internal entrance diameter of approximately 0.160 while its wall thickness was approximately 0.004 inches, its length was 0.875 inches and its inner exit diameter was 0.024 inches. The nozzle is preferably made from any relatively inert material that can be precisely formed or machined such as polypropylene.

It should be noted that the present design can be modified provided the turbulence around the guide tube 16 is minimal after the ultra-pure fluid is passed into the mixing chamber, and that the tip **19*a* of the tube 19** is sufficiently far enough downstream from the center point of the introduction of the carrier fluid to prevent significant concentrations of the injected foreign material to be retained within the chamber after the flow of foreign material into the carrier stream is stopped, thus permitting the mixing chamber to immediately clean itself.

Thus, the present invention comprises a dynamic injection mixing chamber apparatus mounted on an ultra-filtered, ultra-pure chemical delivery system so that test instruments can be connected singly or in multiples to the outputs of the mixing chamber. Pure filtered liquid, such as deionized water, can be introduced through the mixing chamber to become the carrier stream and diluent of the injected concentrate of foreign material. The metered concentrate of foreign material and the carrier stream pass through the mixing nozzle which causes turbulence to thoroughly mix the foreign material in the carrier stream.

In the case of particle counter calibrations and testing, ultra-filtered deionized water was used as the carrier stream and ultra-clean precision syringe and syringe drive a metered certified foreign material stock solution through the injection mixing chamber into the contaminant free deionized water stream. The dilution ratio of the standard to the carrier was set to be nominally one part to a thousand parts. Any incident artifacts in the standard stock solution, and or any generated by the syringe and piping constitute such an insignificant contribution that they can be statistically ignored.

Even the best quality deionized water contains artifacts. For this reason, a 6.4 nanometer dual membrane ultra-filter is used to ensure the deionized water carrier stream contains no artifacts of a size detectable by the particle counters to be calibrated using the present invention. With this type of filtration, it is possible to achieve consistent zero counts even when using a particle counter sensitive to 50 nm particles. Also, the materials used to assemble the injection device are selected to reduce or exclude the creation or injection of artifacts such as may be caused by corrosion, inclusions, and particle shedding. To further guard against background artifact contamination error from the test apparatus, the apparatus is continually flushed with ultra-filtered deionized water as described above.

In one test purchased solutions of PSL spheres were diluted to a concentration of nominally $1 \times 10^7$ spheres per milliliter and stored in a polysulfone bottle. A biocide added to this stock solution prevented bacterial growth and a surface active agent was used to maintain the dispersion of spheres in suspension. Samples were then characterized using a scanning electron microscope (SEM) to determine the actual concentration of spheres. SEM tests of these solutions show them to be remarkably stable over time, with particle concentrations being within the margin of error for the SEM even after 18 months in the case of spheres less than 1000 nm (nanometer) in size. Also, the polysulfone bottles have excellent characteristics for this storage duty as they neither shed particles nor do they pull the PSL spheres out of solution and plate them on the walls of the bottle.

Dynamic serial dilution has enabled a regime which can be used to fairly evaluate any liquid particle counter presently produced. Direct comparisons of up to four particle counters can be made simultaneously with only one stipulation: all of the particle counters being compared must operate at reasonable similar flow rates. This capability has been extremely valuable in making one-to-one comparisons between liquid particle counters.

Simultaneous testing of multiple particle counters is possible because the design of the test apparatus produces fully developed turbulent flow. Injected standard particle suspensions are evenly dispersed in the exiting carrier fluid by the turbulence, created at the mouth of the nozzle to achieve the final serial dilution seen by the particle counters being tested. Since the concentration of particles in the standard suspension has been predetermined with an SEM, all that remains to verify the test concentration is regulation of the carrier flow and adjustment of the injection speed. Precision syringes used as the injector, ranging from 10 to 1000 microliters in total volume, provide a third means of controlling the particle concentration achieved in the final dilution.

Once the dynamic serial dilution apparatus has been installed and the desired sizes of standard particle suspensions have been prepared and certified, testing can progress quickly and smoothly. Precise, repeatable dilutions can be produced without rigorous specialized training.

Figure 3:
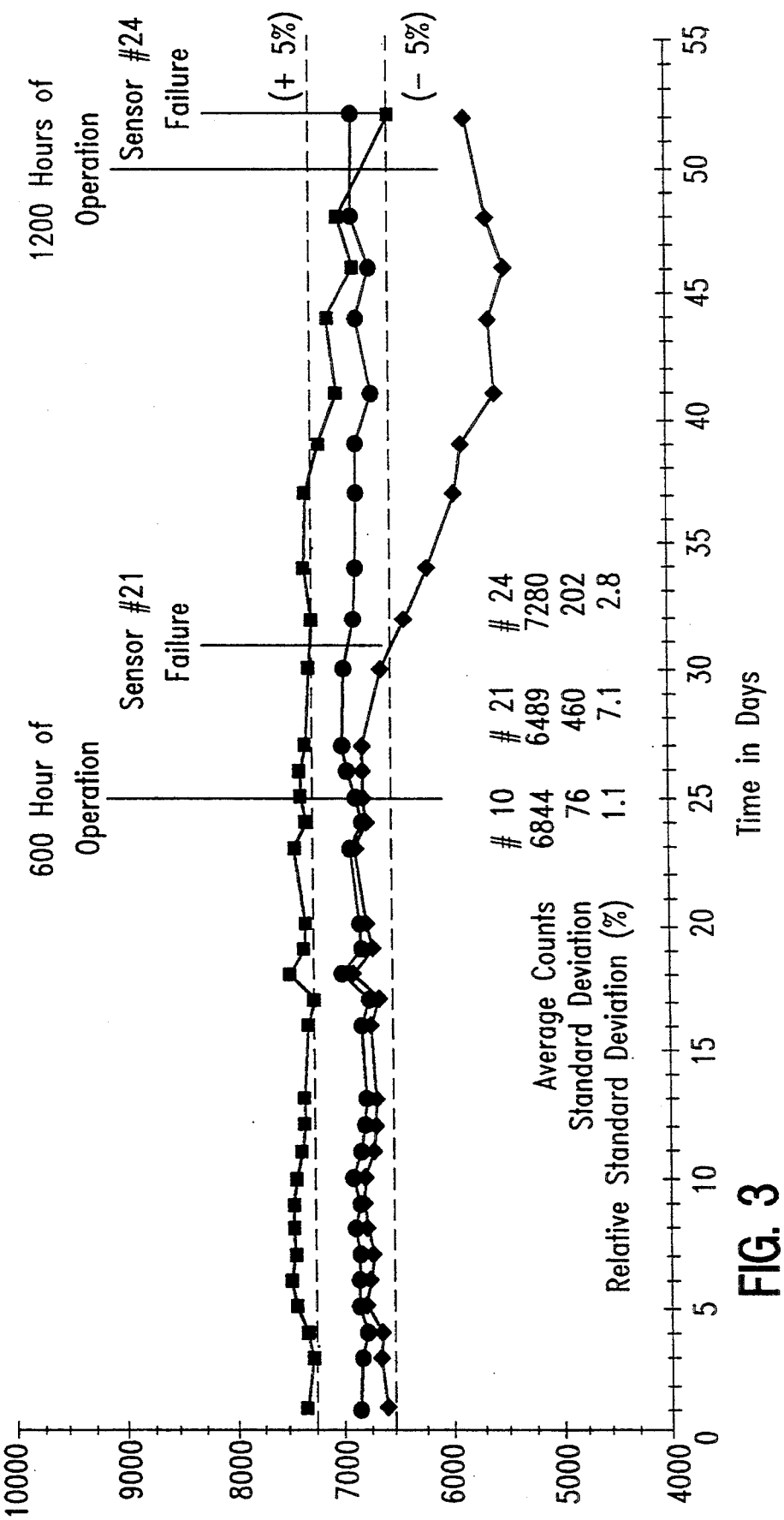
FIG. 3 shows actual test results obtained using the apparatus of FIG. 1.

In one test of interferometric particle counters involving a 1200 hour sustained operation test, thirty-two sample points were collected for each of two particle sizes from three prototype particle counters running in parallel. Each of the sample points consisted of ten runs of ten minutes duration at a flow rate of 40 ml/minute through each particle counter. Two of the particle counters 21 and 24 experienced hardware failures during the test period. The relative standard deviation of the delivered particle concentrations, as measured by Sensor 10, the surviving particle counter, was 1.1% (FIG. 3).

Background counts, counter response to artifacts inherent in the test system, which have always plagued contemporary testing apparatus and methods can essentially be ignored when using the dynamic serial dilution apparatus and method of the present invention. The dual membrane ultra-filter is 99.9% effective at 50 nm and assures the carrier fluid is free of artifacts within the size range of interest. Continual flushing of the entire test apparatus and distribution tubing by the ultra-filtered deionized water prevents artifacts due to shedding or biological contamination from becoming a factor in the background counts.

The standard particle solutions of foreign material being used is tested and verified during the concentration certification by SEM thus eliminating it as a source of uncertainty. A precision syringe can be used as a reservoir from which the standard particle solutions can be injected into the stream, the reservoir or syringe can be cleaned and then their cleanliness verified before use with the particle counters to be tested. Verification of the syringe's condition is accomplished by inserting the syringe needle through the septum of the injection/mixing assembly, and backflushing with the ultra-filtered deionized water, described above, from the carrier fluid stream. The fluid used to backflush the syringe is then injected into the fluid stream at a high volume rate so the syringe is emptied in 15 seconds time. This continued until a count of no more than 50 artifacts is detected after injecting the entire volume of the syringe in 15 seconds into the fluid stream. This assures that there will be no significant background artifacts contributed by the syringe over the course of the normal test period which is approximately two hours.

Acceptance tests conducted on prototype liquid particle counters obtained results that were not only conclusive, but statistically sound.

An example of a typical calibration regime for a particle counter utilized Standard Polystyrene Latex (PSL) spheres of monodisperse size diluted to a certified concentration of 106 spheres per milliliter injected, at a rate of 1 microliter per minute, into a carrier fluid stream flowing at 100 milliliters per minute.

With a minimal investment of money and training, anyone with a consistent supply of clean deionized water can have a repeatable, statistically valid means of calibrating, characterizing, and standardizing all of their liquid particle counters by using the present invention and method described above. Additionally, the dynamic serial dilution apparatus provides a test facility for other instruments designed to measure conditions in a flowing fluid stream, e.g. pH meters, resistivity meters, specific ion monitors, total oxidizable carbon meters, turbidity meters, etc.

The present invention avoids all the present difficulties known to be used with the pump delivery of bulk sample solution at high concentrations. It should now be obvious to one skilled in the art that by varying; the injection rate of the concentrate into the carrier stream, the dilution rate of the concentrate, the size of the input and exit orifices as well as the position of the needle, within certain limits, from those set forth in the above specification without departing from the present invention as set forth in the appended claims.

We claim:

1. A dynamic serial dilution apparatus comprising:

a mixing chamber having an entrance: orifice and an exit orifice;

means for passing a carrier fluid stream through said entrance orifice into said chamber and out of said chamber through said exit orifice;

means for introducing a foreign material into said carrier fluid streaming through said chamber adjacent to said exit orifice, said introducing means comprising an elongated guide tube having a first end portion and an opposite second end portion surrounding and substantially coaxial with an injection tube said injection tube having a first end extending to a position between said entrance orifice and said exit orifice, and a second end extending through a sealing septum, said injection tube being insertable through said septum, said guide tube having a tip at said first end portion adjacent said first end of said injection tube, wherein said first end of said injection tube extends beyond said tip of said guide tube, and wherein said second end portion of said guide tube extends no further than said sealing septum; and a mixing nozzle in said exit orifice.

2. The apparatus of claim 1 wherein said entrance and exit orifices are at least 4 entrance orifice diameters apart, and wherein the tip of said guide tube is positioned a distance of approximately 4 entrance orifice diameters past said entrance orifice towards said exit orifice.

3. The apparatus of claim 1 wherein the tip of said guide tube is positioned at a distance less than 12 entrance orifice diameters past said entrance orifice towards said exit orifice.

4. The apparatus of claim 1 wherein said entrance and exit orifices are at least 7 entrance orifice diameters apart, and wherein said first end of said injection tube is positioned at a distance at least 7 diameters of the entrance orifice from the entrance orifice.

5. The apparatus of claim 1 wherein said first end of said injection tube is positioned at a distance no greater than 15 diameters of the entrance orifice from the entrance orifice.

6. The apparatus of claim 1 wherein said carrier stream in said mixing chamber has a Reynolds number of 500 or less and wherein said first end of said injection tube is positioned in said carrier stream where the stream has a Reynolds number of 500 or less.

7. The apparatus of claim 6 wherein the mixing nozzle has an entrance and an exit diameter to provide the existing fluid stream with a Reynolds number of at least 5000.

8. The apparatus of claim 1 wherein the mixing, nozzle has an entrance diameter substantially equal to the diameter of the exit orifice and an exit diameter approximately equal to 14% of its entrance diameter.

9. The apparatus of claim 8 wherein said mixing nozzle is formed of a relatively inert material.

10. The apparatus of claim 1 wherein said entrance orifice is provided with a filter.

11. The apparatus of claim 1 wherein said mixing chamber is formed of a chemically stable plastic material.

12. The apparatus of claim 1 wherein said means for introducing of foreign material into said carrier fluid comprises a syringe containing a selected concentrate of foreign material to be introduced into the carrier fluid stream.

13. The apparatus of claim 12 wherein said mixing chamber is formed of perfluoroalcoxy, said septum is formed of rubber, and said nozzle is formed of polypropylene.

14. The apparatus of claim 13 wherein said fluid is deionized water.

15. The apparatus of claim 1 wherein said sealing septum is soft and resilient.

* * * * *